United States Patent [19]

Batty, Jr. et al.

[11] Patent Number: 4,550,732
[45] Date of Patent: Nov. 5, 1985

[54] SYSTEM AND PROCESS FOR ENABLING A PREDEFINED FUNCTION WITHIN AN IMPLANTED DEVICE

[75] Inventors: John R. Batty, Jr.; Chester D. Slocum, both of Miami, Fla.

[73] Assignee: Cordis Corporation, Miami, Fla.

[21] Appl. No.: 592,412

[22] Filed: Mar. 23, 1984

[51] Int. Cl.⁴ ............................................. A61N 1/36
[52] U.S. Cl. ........................................... 128/419 PG
[58] Field of Search ................... 128/419 PG, 419 PT

[56] References Cited

U.S. PATENT DOCUMENTS

| 4,124,031 | 11/1978 | Mensink et al. | 128/419 PG |
| 4,164,944 | 8/1979 | Alley, III et al. | 128/419 PG |
| 4,203,447 | 5/1980 | Keller, Jr. et al. | 128/419 PG |
| 4,313,441 | 2/1982 | Buffet | 128/419 PG |

FOREIGN PATENT DOCUMENTS

2826189  1/1979  Fed. Rep. of Germany ...... 128/419 PG

Primary Examiner—William E. Kamm
Attorney, Agent, or Firm—George H. Gerstman

[57] ABSTRACT

A system and process are provided for commanding a device implanted in a patient from an external command unit. A selected routine to be generated in response to a command signal from the external command unit is stored. A first access signal is transmitted from the command unit to the implant, to enable a computer within the implant to receive a command signal. A command signal is transmitted, from the command unit, to operate the selected routine. The operation of the selected routine is inhibited unless both the first access signal and the command signal have been generated.

24 Claims, 7 Drawing Figures

SYSTEM AND PROCESS FOR ENABLING A PREDEFINED FUNCTION WITHIN AN IMPLANTED DEVICE

BACKGROUND OF THE INVENTION

The present invention concerns a novel system for commanding a device implanted in a patient from an external command unit.

Microprocessor-based programmable cardiac pacemakers, which are implanted within the body of a patient, are in wide use today. These pacemakers can be communicated with from an external programmer, to alter the operating parameters of the implanted pacemaker. The pacemakers can be programmed to perform selected operations or to perform a telemetry function by returning information to the external programming device in a selected manner.

Some prior art programmable pacers are communicated with through a serial binary code format. Various transmission methods are used to transmit the binary code, such as magnetic reed switch, ultrasound, infrared signals, radio frequency pulses and bursts, amplitude modulation and frequency modulation.

The proper function of the communication link is of utmost importance to the operation of the pacer and ultimately to the well-being of the patient. There is a concern that the communication link may be affected by improper external sources, such as electromagnetic radiation emitted from various sources including therapeutic equipment. In addition, there may be improper interference from a programming code emitted by a programming device that is not intended to be used with the particular pacer that is implanted in the patient.

Certain prior art units include a read switch enabling the programming circuit to operate. The reed switch operates as a simple switch which is closed by the application of a magnetic field. The reed switch is in the implant and an external magnet closes the switch to commence the operation. One method of programming is by external magnetic pulsations which force the reed switch to open and close to provide the data signals to the implant circuitry.

In U.S. Pat. No. 4,361,153, assigned to the assignee of the present invention, a system is described in which a carrier signal from the programmer is transmitted to a tank circuit inthe implant. The tank circuit reflects back to the external programmer a wave formed with the signal data impressed thereon. The signal data is derived from a microprocessor which is coupled to sensors for various pacer functions such as rate, battery level, etc. If it is desired to change a function of the implanted pacer, the implant tank circuit acts as an antenna and receives the information. Instead of being reflected with signal data that is provided to the tank circuit, it is coupled to the microprocessor for providing the signals to the microprocessor which were received from the external programming circuit for making the desired change.

While the programming and telemetry system may be relatively complicated, it is desirable to be able to effect a simple command from an external source, to perform a selected routine. For example, if a patient simply wants to determine the battery condition of the pacer, the use of complex programming or telemetry should not be required. There are many selected routines which are relatively simple and which may be desired without the requirement of complex programming or telemetry. For example, as stated above, the patient or physician may want to take the pacer out of its sensing mode and simply check the implant battery. In another routine, the physician may simply wish to place the pacer into a temporary special pulse rate. As another possible routine, the physician may want to simply place the pacer into a temporary overdrive routine.

It is thus desirable to have the ability to provide an external command, and from this external command enable a predefined function within the implanted pacer.

It is desirable to provide a system in which a predefined function within the pacer can be enabled, without the use of a magnetic reed switch.

It is, therefore, an object of the present invention to provide a system in which a relatively simple external command device may be provided for commanding the implanted pacer to execute a selected function.

It is also an object of the present invention to provide security so that the command signal that is being transmitted from the external source to the implant is the proper command signal from the external command unit rather than some extraneous signal or rather than a signal from an improper command unit.

BRIEF DESCRIPTION OF THE INVENTION

In accordance with the present invention, a system is provided for commanding a device implanted in a patient from an external command unit. The improvement comprises an implanted device having means for receiving external signals, means for receiving an external command signal, means for storing a selected routine to be operated in response to a command signal from the external command unit, means for decoding a first access signal to prevent access to the routine storing means unless the first access signal is received, and means for detecting a command signal to prevent access to the routine storing means unless both the first access signal and the command signal are received.

In the illustrative embodiment, the implanted device is a cardiac pacer. The means for receiving external access signals comprises an induction coil and the means for receiving external command signals comprises the input of a microprocessor.

In the illustrative embodiment, an external command unit is provided comprising a pulse generator for generating the first access signal and the command signals. The first access signal comprises a pulse width modulated binary code and the command signal comprises a pulse having a width that is greater than any of the pulses of the first access signal. The command signal is operative to enable the selected routine that is stored by the routine storing means. The selected routine is enabled until the occurrence of a predetermined event. In the illustrative embodiment, the predetermined event comprises the lack of pulse activity received by the external command signal receiving means for a predetermined amount of time. The external command unit is operative to repeat the first access signals cyclically for enabling the selected routine.

In accordance with the present invention, a process is provided for commanding a device implanted in a patient from an external command unit. The process comprises the steps of storing a selected routine to be operated in response to a command signal from the external command unit; transmitting, from the command unit to the implant, a first access signal to enable a computer within the implant to receive a command signal; transmitting, from the command unit, a command signal to operate the selected routine; and inhibiting the operation of the selected routine unless both the first access signal and the command signal have been generated.

A more detailed explanation of the invention is provided in the following description and claims, and is illustrated in the accompanying drawings.

DETAILED DESCRIPTION OF THE ILLUSTRATIVE EMBODIMENT

Figure 1:
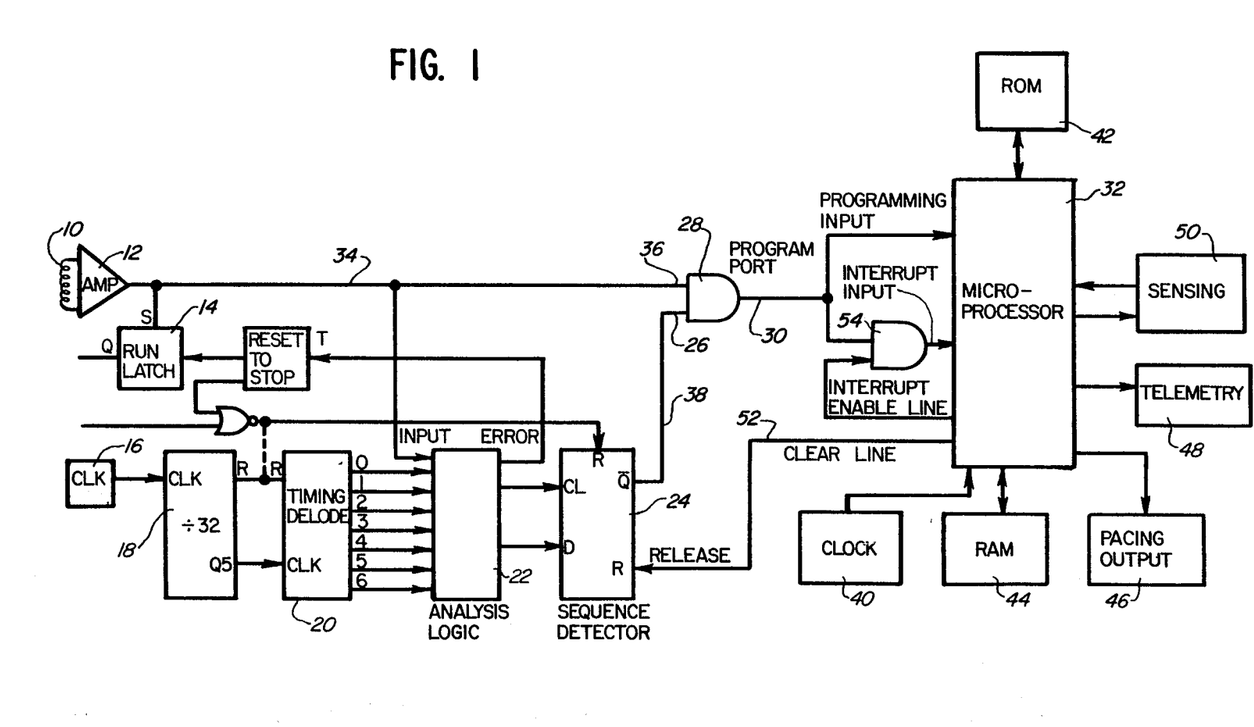
FIG. 1 is a schematic block diagram of an implanted portion of a system for commanding a device implanted in a patient from an external command unit, constructed in accordance with the principles of the present invention.

Referring to FIG. 1, a schematic block diagram of the circuitry within the implanted pacer is illustrated therein. Although no limitation is intended, the circuit of the present invention may be fabricated on a CMOS digital logic array chip such as an Advanced Micro-circuits Corporation Q 411 "Quick Chip" with an equivalent gate count of 500. This circuit will operate over the voltage range of 3 to 5 volts at a typical current drain of about one microamp.

Figure 2:
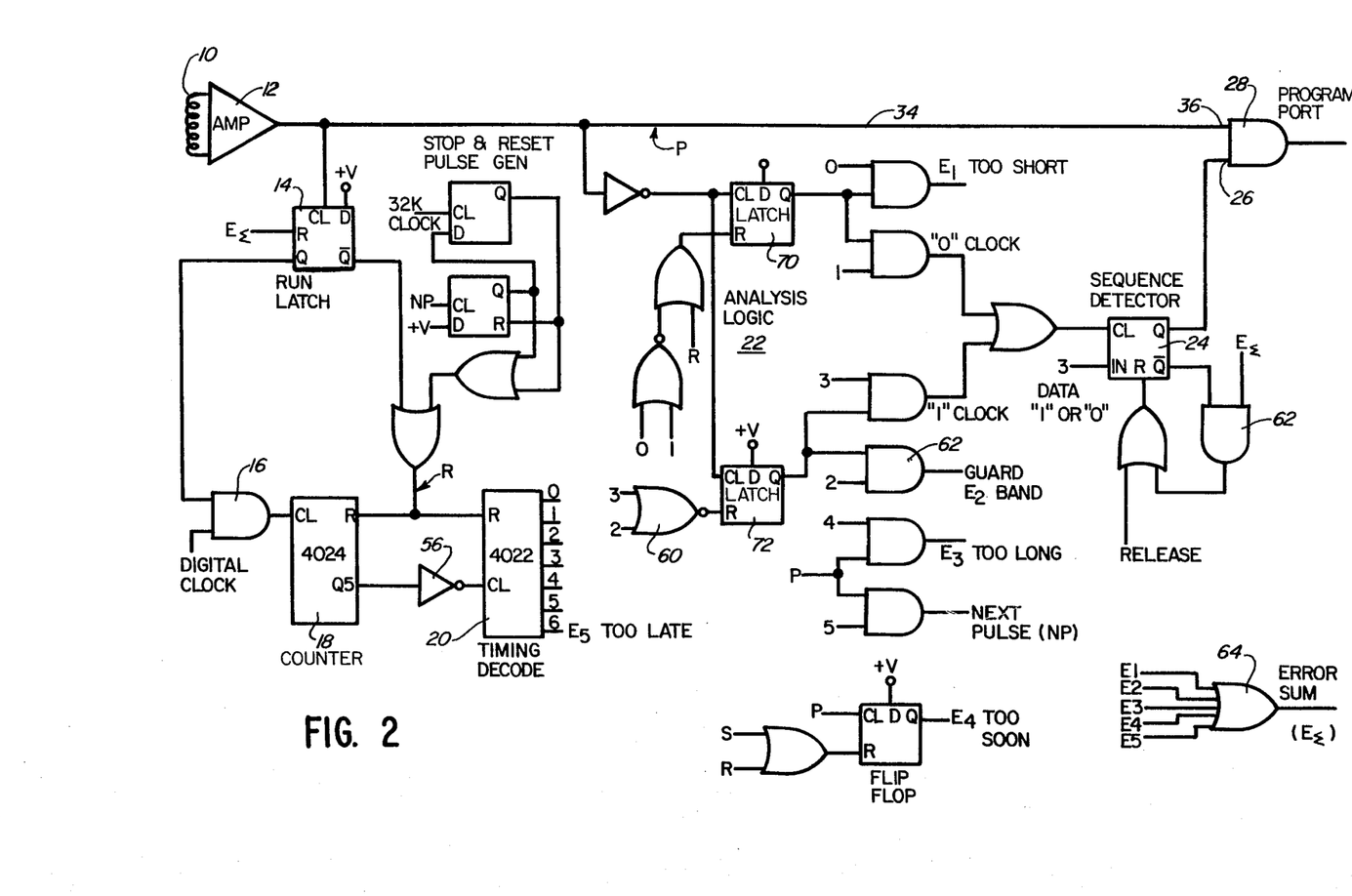
FIG. 2 is a schematic logic diagram of the decoding portion of the circuit of FIG. 1.
Figure 3:
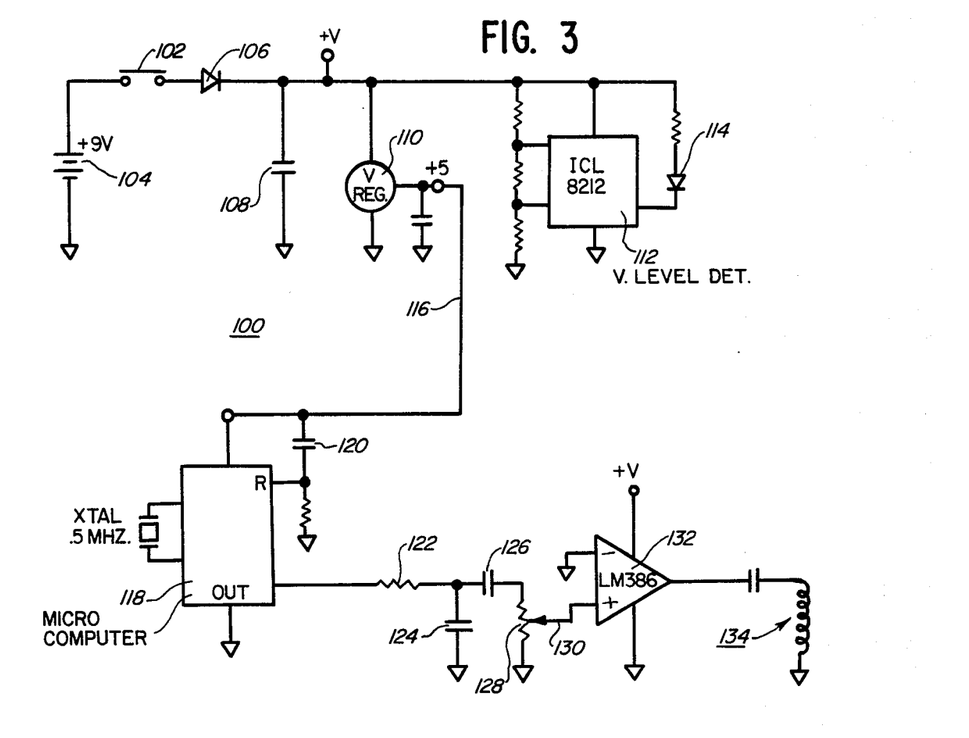
FIG. 3 is a schematic circuit diagram of an external command unit constructed in accordance with the principles of the present invention and usable with the implanted circuitry of FIG. 1.

As seen in FIG. 1, the packer's circuitry includes an induction coil 10 for receiving access signals and command signals from an external command unit 100 (FIG. 3). The signals are amplified by amplifier 12, integrated, and the first edge of the input pulse sets latch 14 to wake up the system. In order to save power, divide by thirty-two counter 18 is normally held reset. The clock 16 and activated counter 18 provide an input to a Johnson counter 20 to provide decoding windows. The decoding windows, which are pulses provided on one of seven output lines depending upon the code, are inputted to an analysis logic circuit 22 which comprises a series of combination and sequential logic elements shown in more detail on FIG. 2. The output of analysis logic circuit 22 is fed to a sequence detector 24, the output of which is fed to an input 26 of transmission AND gate 28. The output 30 of AND gate 28 is connected to the programming input of microprocessor 32. The access signals and the command signals are fed via lines 34 to the other input 36 of AND gate 28.

It can be seen that in order to access the programming input of microprocessor 32, a first proper access code is required. If the sequence detector 24 outputs a high via line 38 to input 26 of AND gate 28, signals on line 34 can be transmitted to the programming input of microprocessor 32. The first access code which is used to access the programming input of microprocessor 32 is transmitted at a relatively slow rate (180 baud). However, once the programming input of microprocessor 32 is accessed, a second access code, which is transmitted at a relatively fast rate (330 baud) is required to achieve operative communication between the programming circuit and the pacer. To this end, a software routine is utilized for analyzing the second access code and for rechecking in order to be certain that the second access code is proper.

The first access code may be referred to as the PAD (program access decoder) code and the second access code may be referred to as the I.D. (identification code). These codes are preferably digital codes in the form of pulse width modulated signals.

However, the present invention provides a system by which a selected routine may be operated as a result of the transmission of a command signal. If a proper second access code is utilized, operative communication between the programming circuit and the pacer will be achieved. On the other hand, if a special command signal is provided instead of using the second access code, the pacer will be programmed into its "magnet mode" and continue in this magnet mode until there is lack of pulse activity for a predetermined amount of time.

It can be seen that in order to operate a selected routine in response to an external command signal, the PAD code is first required. This will access the programming input of microprocessor 32, and once the programming input of microprocessor 32 is accessed, the command signal is required to place the pacer into its magnet rate and operate a selected routine which has been preselected for operation in response to reception of the command signal.

Microprocessor 32 is clocked by means of clock 40. The program for microprocessor 32 is stored in ROM 42 and microprocessor 32 is coupled to RAMs 44 for temporary storage. The microprocessor has output functions including the pacing output pulse generator 46, telemetry output 48 and sensing function 50, all of which output functions are well-known in the art. There is a clear line 52 from microprocessor to sequence detector 24 to clear sequence detector 24 when communication is finished or there has been an error detected. If an error has been detected, microprocessor 32 will clear sequence detector 24 via clear line 52.

Microprocessor 32 normally enables an AND gate 54. However, if the PAD code has been received, i.e., if the first access signal has been received, microprocessor 32 will interrupt its normal output functioning so that it can receive programming or command information via line 34.

Microprocessor 32 controls the sensing hardware and also receives information from the sensing hardware. Microprocessor 32 also controls telemetry circuit 48 for example, by causing the variation in the impedance in the tank coil. Microprocessor 32 also controls the pacing output 46 which includes the rate of fixed stimulation.

A more detailed illustration of the logic circuitry is found in FIG. 2. In FIG. 2, identical reference numerals as in FIG. 1 are used to indicate identical items.

Referring to FIG. 2, it can be seen that clock 16 is outputted to a 4024 divide by thirty-two counter, the output of which is connected through inverter 56 to the clock input of a 4022 Johnson counter. Only seven of the Johnson counter outputs are used. The numbers represent the state provided by the counter outputs, with, for example, counter output 2 being at an input to NOR gate 60 and also at an input to AND gate 62. The number 6 output from Johnson counter 20 is E5 which is fed to the error sum OR gate 64. The output of the error sum OR gate 64 is fed to the reset input of the run latch 14 and also to an input of the AND gate 66 coupled to the sequence detector 24 which is made up of a pair of flip-flops. By noting the numbers at the inputs of the AND gates, OR gates, NOR gates and flip-flops, it can be seen how the corresponding numbered outputs of Johnson counter 20 provide the appropriate windows to form a pulse width and period detector.

Thus the first rising edge of the input data sets the run latch 14 which releases the resets from all counters and latches in the circuit. The run latch allows the counters to time and gate the analysis latch. Divider 18 generates a 1024 hertz (976 microseconds) clock to advance the timing decoder 20 which forms six time slots that the input signal can be checked with for validity and value (0 or 1). Latches 70 and 72 are used to detect the falling edges of input data and decode the conditions E1, 0,E2 or 1. The reset logic to the latches is used to initialize and enable the latches at the appropriate times. The other gates are used to decode the conditions E3, next pulse and E4. All error (E) signals are used to produce the error sum signal. Thus, this circuitry analyzes input pulses and decides whether the pulses will have the proper width (0 or 1) and the proper period. Any error resets the entire system to terminate. As the bits are analyzed, they are inputted to the sequence detector, After the proper code sequence has been received, all future data is gated to the program port.

Figure 5:
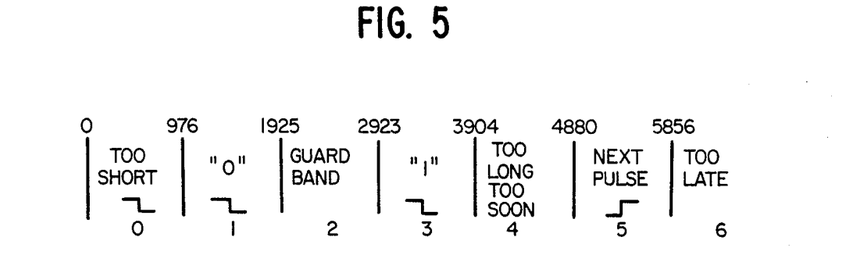
FIG. 5 is a diagram showing the timing windows of the system of FIG. 1.

The timing windows for the system are illustrated in FIG. 5. The numbers at the bottom of FIG. 5 (0 through 6) correspond to the numbers on the output lines of Johnson counter 20. Thus if the pulse drop is seen between 0 and 976 microseconds, there is an output from the analysis logic 22 indicating error 1 (too short). If the pulse drop is seen between 976 and 1925 microseconds, it is determined to be a "0". If the pulse drop is seen between 2928 microseconds and 3904 microseconds, it is determined to be a "1." If the pulse drop is seen at other times as indicated in FIG. 5, error signals are detected.

Figure 6:
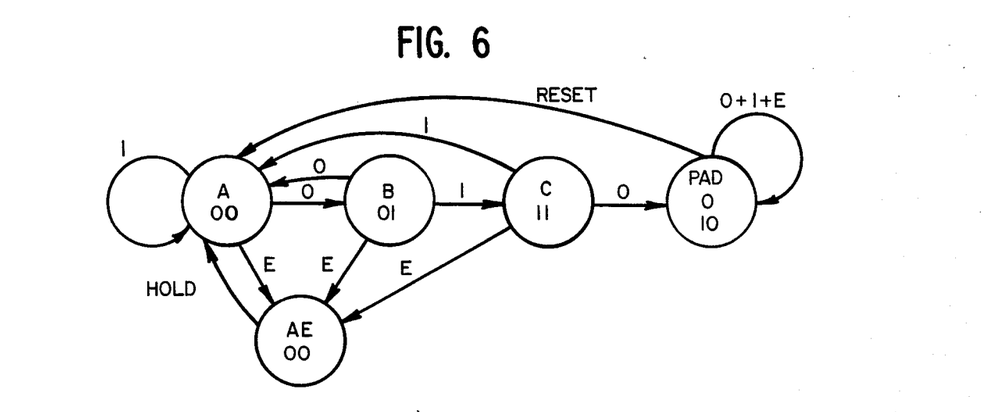
FIG. 6 is a diagram showing the operational states of the sequence detector of FIGS. 1 and 2.

FIG. 6 is the state diagram for the sequence detector for a binary code of 010. Begin at state A. If a zero is received, advance to state B. Thereafter, if a one is received, advance to state C. If a zero is received, advance to state D which unlocks the programming circuit and latches the system so that it awaits the I.D. code or the command signal for the pacer until it is reset by the microprocessor. It can be seen that if the system is in state B and a zero is received instead of a one, it reverts to a state A. Likewise, if the system is in state C and receives a one instead of a zero, it reverts to state A. Once the system reaches state D, a reset signal reverts the system to state A. "Hold" is the rest position of the system. Invalid timing causes an error signal (E) and the system enters into state AE. Once the system reverts to state A, new data can be entered into the detector.

The circuitry for the external command unit is illustrated in FIG. 3. Referring to FIG. 3, it can be seen that external command unit circuit 100 includes a manually-operable switch 102 which acts as a command switch to energize the system from a 9-volt battery 104. The circuit includes a rectifier 106, a filter capacitor 108, a voltage regulator 110 to provide, for example, five volts DC, a voltage lever detector 112 operative to indicate the voltage level of battery 104, and a light-emitting diode 114 which indicates the voltage condition of battery 104 to the operator.

Figure 4:
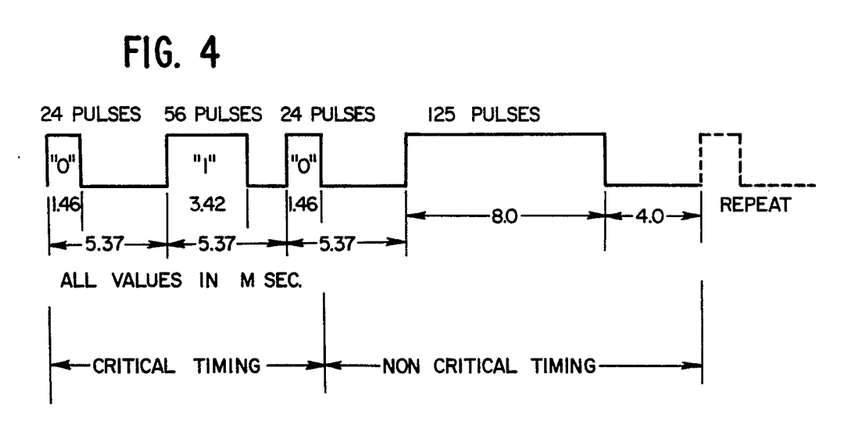
FIG. 4 is a pulse timing diagram of the output from the FIG. 3 circuit.

The five-volt output is coupled via line 115 to a microcomputer 118 which operates to generate the PAD code and a long pulse, with the pulse timing diagram being illustrated in FIG. 4. A capacitor 120 is used to act as a power-on reset and a resistor 122-capacitor 124 combination is provided as a low pass filter or integrator to round the pulses. A capacitor 126 and potentiometer 128 combination is provided and used as a high pass filter or differentiator to filter out the DC and to act as an output level or drive level control. Arm 130 of potentiometer 128 is coupled to the positive input of amplifier 132, the output of which is connected to a series resonant tuned coil load 134.

When coil load 134 of external command unit circuit 100 is placed in an inductive relationship with implant coil 10 (FIGS. 1 and 2) and switch 102 is activated by the operator, the external command unit will transmit the pulses illustrated in FIG. 4. The first three pulses comprise the PAD code, in the form of a pulse width modulated binary code, with the PAD code in the illustrative embodiment being 010. As illustrated in FIG. 4, each of the pulses representing a binary bit is actually in envelope containing a number of pulses. After the PAD code is issued, a relatively long command pulse will be transmitted. In the illustrative embodiment, the command pulse comprises an envelope containing 125 pulses, which is substantially longer than the pulse envelopes representing the binary bits. The PAD code and command signal will continue to repeat so long as the operator wants the pacer to be in its magnet mode with the selected function in operation.

Figure 7:
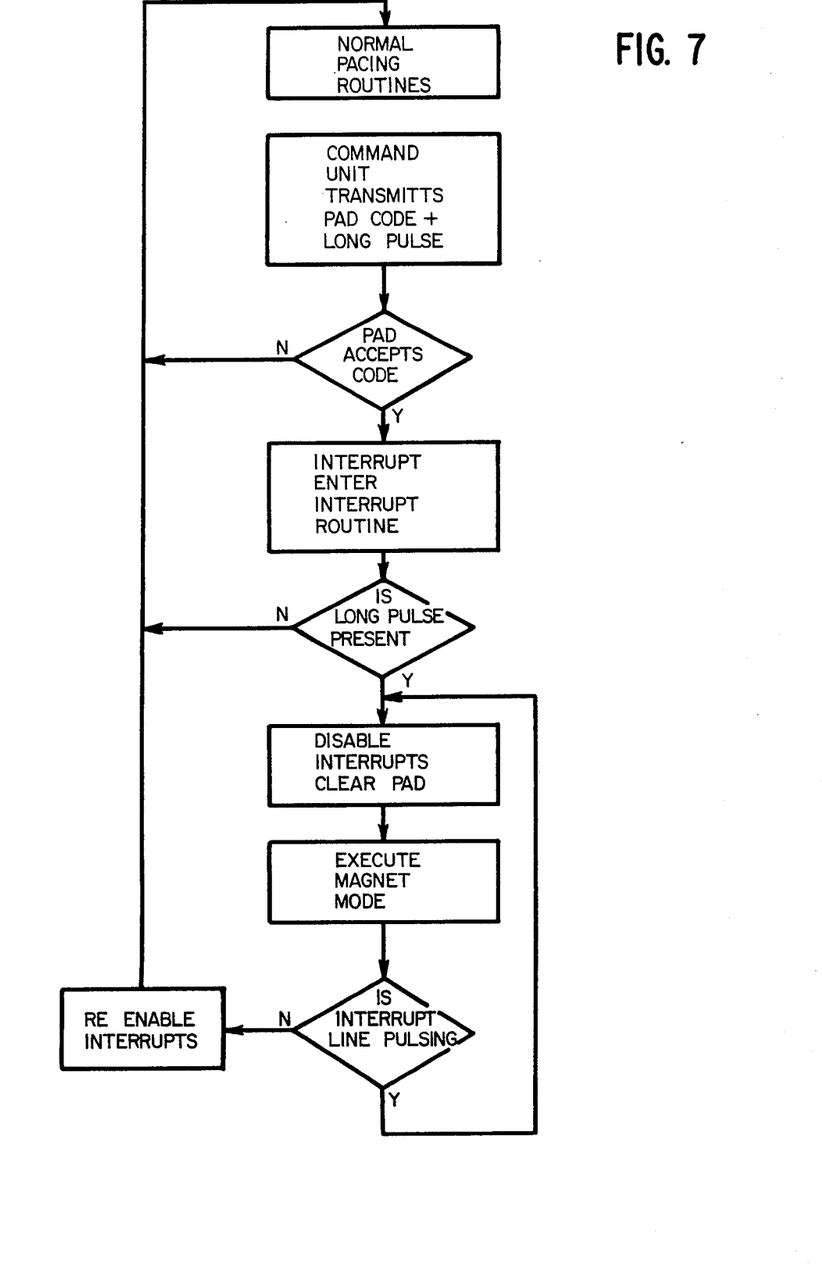
FIG. 7 is a flow chart illustrating the steps of a system in a process for commanding a device implanted in a patient from an external command unit, in accordance with the principles of the present invention.

With reference to FIG. 7, a flow chart is provided for illustrating the operation of the system. In use, the user places the external command unit on the patient's skin above the implanted pacer. The user presses and holds down button 102 and then the command unit transmits the PAD code and the long pulse. If the PAD code is accepted, a signal at AND gate 54 (FIG. 1) will commence the interrupt routine for the microprocessor. In this manner, the microprocessor looks at its programming input to determine if the long pulse is present. If the long pulse is present, the interrupt routine is disabled and the program port is cleared to receive another PAD code. Once the PAD code and long pulse are received, the magnet mode of the microprocessor will be in effect and will continue unless there is more than a 4-millisecond gap without any pulses. In other words, so long as there are pulses within any 4-millisecond gap, the magnet mode will continue. During presence of the magnet mode, the preselected function will function. As stated previously, the preselected function could be a routine taking the pacer out of its sensing mode and checking the implant battery. Alternatively, the preselected function could be the placing of a pacer into a temporary special pulse rate. Alternatively, the preselected routine could be the placing of the pacer into a temporary overdrive routine.

If there is no pulse activity for more than four milliseconds, the interrupt will be reenabled and the system will return to its normal pacing routines.

It can be seen that a system has been provided for commanding a device implanted in a patient from an external command unit, with a security code operating to function as a key to unlock the system. In the illustrative embodiment, a first access code is required to unlock a transmission gate upstream of the microprocessor in the implanted pacer in addition to a command signal that is required to operate a preselected function.

Although an illustrative embodiment of the invention has been shown and described, it is to be understood that various modifications and substitutions may be made by those skilled in the art without departing from the novel spirit and scope of the present invention.

What is claimed is:

1. A system for enabling a predefined function within a device implanted in a patient from an external command unit, comprising:
    an external command unit for generating external signals including a first access signal and a command signal;
    an implanted device having means for receiving external signals, means for receiving external command signals, means for storing a temporarily operated selected routine to be generated in response to a command signal from the external command unit, means for decoding the first access signal to prevent access to the routine storing means unless the first access signal is received, and means for detecting the command signal to prevent access to the routine storing unless both the first access signal and the command signal are received, whereby the temporarily operated selected routine is generated only if both the first access signal and the command signal are received.

2. In a system as described in claim 1, wherein the implanted device is a cardiac pacer including a pacing output pulse generator.

3. In a system as described in claim 1, wherein the means for receiving external signals comprises an induction coil.

4. In a system as described in claim 1, including a microprocessor for operating said selected routine and wherein the means for receiving external command signals comprises the input of said microprocessor.

5. In a system as described in claim 1, including an external command unit comprising a pulse generator for generating said first access signals and said command signals.

6. In a system as described in claim 5, said first access signal comprising pulses of a pulse width modulated binary code and said command signal comprising a pulse having a width that is greater than any of the pulses of said first access signal.

7. In a system as described in claim 6, said pulses each comprising an envelope containing a plurality of pulses.

8. In a system as described in claim 5, said first access signal comprising pulses of a pulse width modulated binary code; said command signal being operative to enable the selected routine stored by the routine storing means.

9. In a system as described in claim 1, including means for enabling the selected routine until the occurrence of a predetermined event.

10. In a system as described in claim 9, said predetermined event comprising the lack of pulse activity received by said external signals receiving means for a predetermined amount of time, and including means for detecting said lack of pulse activity.

11. In a system as described in claim 8, including means for enabling said external command unit to continue to generate pulses for enabling the selected routine.

12. In a system as described in claim 11, including means for enabling said external command unit to repeat the first access signal and the command signal cyclically for enabling the selected routine.

13. In a system as described in claim 12, including means for enabling said external command unit to discontinue the generation of pulses to terminate the selected routine.

14. In a system as described in claim 12, said command signal comprising a pulse having a width that is greater than any of the pulses of said first access signal.

15. A system as described in claim 1, wherein both said first access signal and said command signal comprise electromagnetic waveforms.

16. A system for enabling a predefined function within a cardiac pacer implanted in a patient from an external command unit, comprising:
    an external command unit for generating external signals including a first access signal and a command signal;
    an implanted device having an induction coil for receiving external signals, a microprocessor for operating said selected routine and having a microprocessor input for receiving external command signals, means for storing a temporarily operated selected routine to be generated in response to a command signal from the external command unit, means for decoding the first access signal to prevent access to the routine storing means unless the first access signal is received, and means for detecting the command signal to prevent access to the routine storing means unless both a first access signal and the command signal are received whereby the temporarily operated selected routine is generated only if both the first access signal and the command signal are received;
    said external command unit comprising a pulse generator for generating said first access signal and said command signal;
    said first access signal comprising pulses of a pulse width modulated binary code;
    said command signal being operative to enable the selected routine stored by the routine storing means, the selected routine being enabled until the occurrence of a predetermined event, the predetermined event comprising the lack of pulse activity received by said external command signal receiving means for a predetermined amount of time.

17. In a system as described in claim 16, including means for enabling said external command unit to repeat the first access signal and the command signal cyclically for enabling the selected routine.

18. In a system as described in claim 17, including means for enabling said external command unit to discontinue the generation of pulses to terminate the selected routine.

19. A process for enabling a predefined function within a device implanted in a patient from an external command unit, comprising the steps of:
    storing a temporarily operated selected routine to be generated in response to a command signal from the external command unit;
    thereafter transmitting, from the command unit to the implant, a first access signal for enabling a computer within the implant to receive a command signal when the first access signal is detected;

thereafter transmitting, from the command unit, a command signal that is different than the first access signal to operate said selected routine; and inhibiting the operation of said selected routine unless both the first access signal and the command signal have been generated, whereby the temporarily operated selected routine is generated only if both the first access signal and the command signal are received.

20. A process as described in claim 19, in which said first access signal comprises a pulse width modulated binary code and said command signal comprises a pulse having a width that is greater than any of the pulses of said first access signal.

21. A process as described in claim 19, including the step of operating the selected routine until a lack of signal activity is detected.

22. A process as described in claim 19, including the step of operating the selected routine by continuing the generation of pulses, the step of discontinuing the selected routine by discontinuing the generation of pulses over a predetermined period of time, and the step of detecting whether pulses are being generated.

23. A process as described in claim 19, including the step of transmitting the first access signal and the command signal cyclically for operating the selected routine.

24. A process for enabling a predefined function within a device implanted in a patient from an external command unit, comprising the steps of:

storing a temporarily operated selected routine to be generated in response to a command signal from the external command unit;

thereafter transmitting, from the command unit to the implant, a first access signal for enabling a computer within the implant to receive a command signal when the first access signal is detected;

thereafter transmitting, from the command unit, a command signal that is different than the first access signal to operate said selected routine;

said first access signal comprises pulses of a pulse width modulated binary code and said command signal comprising a pulse having a width that is greater than any of the pulses of said first access signal;

operating the selected routine by continuing the generation of pulses;

discontinuing the selected routine by discontinuing the generation of pulses over a predetermined period of time;

transmitting the first access signal and the command signal cyclically for operating the selected routine; and inhibiting the operation of said selected routine unless both the first access signal and the command signal have been generated, whereby the temporarily operated selected routine is generated only if both the first access signal and the command signal are received.

* * * * *